(12) United States Patent  
Heide et al.

(10) Patent No.: US 9,322,729 B2  
(45) Date of Patent: Apr. 26, 2016

(54) METHOD AND DEVICE FOR DETERMINING THE PRESSURE OR VOLUMETRIC FLOW OF MEDICAL FLUIDS

(75) Inventors: Alexander Heide, Eppstein (DE); Robin Partenfelder, Oberursel (DE); Arne Peters, Bad Homburg (DE); Christoph Wiktor, Gelnhausen (DE); Juergen Klewinghaus, Oberursel (DE)

(73) Assignee: Fresenius Medical Care Deutschland GmbH, Bad Homburg (DE)

( * ) Notice: Subject to any disclaimer, the term of this patent is extended or adjusted under 35 U.S.C. 154(b) by 552 days.

(21) Appl. No.: 13/635,485

(22) PCT Filed: Mar. 16, 2011

(86) PCT No.: PCT/EP2011/001300

§ 371 (c)(1),  
(2), (4) Date: Oct. 18, 2012

(87) PCT Pub. No.: WO2011/113588

PCT Pub. Date: Sep. 22, 2011

(65) Prior Publication Data

US 2013/0072846 A1    Mar. 21, 2013

(30) Foreign Application Priority Data

Mar. 17, 2010    (DE) .......................... 10 2010 011 798

(51) Int. Cl.  
*A61M 37/00* (2006.01)  
*G01L 7/00* (2006.01)  
(Continued)

(52) U.S. Cl.  
CPC ................. *G01L 7/00* (2013.01); *A61M 1/101* (2013.01); *A61M 1/1086* (2013.01);  
(Continued)

(58) Field of Classification Search  
CPC ............ A61M 1/3639; A61M 1/3621; A61M 2205/3355; A61M 2205/3351; A61M 2205/3365; A61M 2205/3334

USPC .................................. 604/6.09, 6.11; 210/646  
See application file for complete search history.

(56) References Cited

U.S. PATENT DOCUMENTS 613,395 A * 11/1898 Perfler et al. ................ 235/60.37  
6,048,363 A * 4/2000 Nagyszalanczy et al. ... 623/3.13  
(Continued)

FOREIGN PATENT DOCUMENTS

DE    196 45 129 A1    5/1998  
DE    198 40 399 A1    3/1999  
(Continued)

OTHER PUBLICATIONS

International Search Report from PCT/EP2011/001300 mailed on Aug. 19, 2011.  
www.wikipedia.de "Kreiselpumpe" (Chapter: Eigenschaften), 2010.

*Primary Examiner* — Leslie Deak  
(74) *Attorney, Agent, or Firm* — Kenyon & Kenyon LLP

(57) ABSTRACT

A method for determining a pressure of a medical fluid in a fluid line by using at least one centrifugal pump includes detecting the pressure upstream of the centrifugal pump while considering an information about a pressure downstream of the centrifugal pump, or detecting the pressure downstream of the centrifugal pump while considering an information about a pressure upstream of the centrifugal pump. Thereby, at least one information about the volume flow in the fluid line and/or at least one information about a rotation speed of the centrifugal pump are considered, respectively. The invention also relates to a method for determining a volume flow, an arithmetic unit, a treatment apparatus, a digital storage means, a computer program product and a computer program.

15 Claims, 3 Drawing Sheets

(51) Int. Cl.
*A61M 1/10* (2006.01)
*A61M 1/36* (2006.01)
*F04D 15/00* (2006.01)
*F04D 29/00* (2006.01)
*G06F 19/00* (2011.01)

(52) U.S. Cl.
CPC .......... *A61M 1/3621* (2013.01); *A61M 1/3639* (2013.01); *F04D 15/0088* (2013.01); *F04D 29/00* (2013.01); *G06F 19/00* (2013.01); *A61M 2205/3334* (2013.01); *A61M 2205/3351* (2013.01); *A61M 2205/3355* (2013.01); *A61M 2205/3365* (2013.01)

(56) References Cited

U.S. PATENT DOCUMENTS

| | | | | |
|---|---|---|---|---|
| 6,148,354 | A | * | 11/2000 | Ban et al. ....................... 710/301 |
| 6,564,627 | B1 | * | 5/2003 | Sabini et al. .................... 73/168 |
| 2008/0199357 | A1 | * | 8/2008 | Gellman et al. ................. 422/48 |
| 2009/0124963 | A1 | * | 5/2009 | Hogard et al. .................. 604/30 |

FOREIGN PATENT DOCUMENTS

| | | |
|---|---|---|
| DE | 10 2009 027 195 A1 | 12/2010 |
| EP | 1 284 369 A1 | 2/2003 |
| WO | 2005/085772 A1 | 9/2005 |
| WO | 2010/149408 A1 | 12/2010 |

* cited by examiner

METHOD AND DEVICE FOR DETERMINING THE PRESSURE OR VOLUMETRIC FLOW OF MEDICAL FLUIDS

CROSS REFERENCE TO RELATED APPLICATIONS

The present application is the national stage entry of International Patent Application No. PCT/EP2011/001300, filed on Mar. 16, 2011, and claims priority to Application No. DE 10 2010 011 798.6, filed in the Federal Republic of Germany on Mar. 17, 2010.

FIELD OF INVENTION

The present invention relates to a method for determining a pressure of a medical fluid in a volume flow of the fluid by using at least one centrifugal pump. It further relates to a method for determining a volume flow or flux of the fluid. Furthermore, it relates to an external medical functional device, an arithmetic unit, a treatment apparatus, a digital storage means, a computer program product and a computer program.

BACKGROUND

In practice, the pressure present in a volume flow of a fluid or in a fluid line is measured in different ways.

SUMMARY

One object of the present invention is to provide a method for determination or determining, respectively, a pressure of a medical fluid in a volume flow of the fluid or in a fluid line by using at least one centrifugal pump.

The method according to the invention comprises detecting the pressure upstream of the centrifugal pump or an impeller pump while considering an information about a pressure downstream of the centrifugal pump or detecting the pressure downstream of the centrifugal pump or an impeller pump while considering an information about a pressure upstream of the centrifugal pump. In each of these cases, the method according to the invention comprises considering an information about the volume flow in the fluid line and/or an information about at least one rotation speed of the centrifugal pump.

A further object of the present invention is to provide a method for the determination or determining, respectively, a volume flow of a medical fluid in a fluid line by using at least one centrifugal pump.

The method according to the invention comprises detecting the volume flow in the fluid line or an information thereabout while considering the pressure upstream and the pressure downstream of the centrifugal pump as well as at least one information about a rotation speed of the centrifugal pump.

Exemplary embodiments according to the invention can each comprise one or more of the following features.

In all of the following exemplary embodiments, the use of the term "can be" or "can have" or "can comprise", respectively, etc. is to be understood as a synonym for "preferably is" or "preferably has" or "preferably comprises", respectively, etc. and shall exemplify an embodiment according to the invention.

The term "pressure" as used herein is in one embodiment according to the invention to be understood as the static pressure of the fluid (also referred to as hydrostatic pressure) in the volume flow or in the fluid line.

In another embodiment according to the invention, the "pressure" is to be understood as the dynamic portion (also referred to as the hydrodynamic pressure) of the fluid.

The static pressure can be measured by means of appropriate pressure sensors or pressure pickups known from state of the art. Examples of such pressure sensors are piezoelectric pressure sensors or pressure sensors comprising strain gauges.

In some exemplary embodiments according to the method of the present invention, determining a pressure is to be understood as calculating the pressure or estimating the pressure based on mathematic formulas with sufficiently good approximation, or the like.

The term "medical fluid" as used herein is understood to be blood, dialysate, substituate or any other medical fluid. Among those are, for example, also fluids for cleaning a tubing or circuit prior to or after an application, for filling prior to an application ("priming volume"). Furthermore, medical fluids also comprise dialysate liquids, solved substances such as electrolytes (sodium, potassium, calcium, magnesium), buffers (lactate or bicarbonate), sugar (glucose), and the like. A medical fluid can also be an appropriate combination of some of the fluids mentioned above.

In the context of the present invention, centrifugal pumps may, for example, be embodied as radial pumps, diagonal or semi-axial pumps or axial pumps.

The terms "upstream" and "downstream" of the centrifugal pump refer to the throughflow direction of the centrifugal pump or to the inflow or outflow, respectively, direction of the medical fluid in relation to the centrifugal pump.

"Upstream" refers to positions or sites, respectively, or states ahead of the throughflowing of the centrifugal pump, i.e., before the pump inlet. This can be a site within the inflow line immediately in front of the pump inlet, e.g., 1 cm, 5 cm, 10 cm in front of the centrifugal pump, or a site having a longer distance to the pump inlet, e.g., 50 cm or 100 cm, or a site having a distance between these values/distances in front of the centrifugal pump.

"Downstream" refers to positions or sites, respectively, and states after having flown through the centrifugal pump, i.e., a site within the outflow line after the pump outlet. As regards the distances, the same applies as given for "upstream". The pressure downstream is usually also referred to as post-pump pressure.

In the context of the present invention, an information about the volume flow can be detected in different ways. For example, an information can be obtained or measured, respectively, by means of appropriate volume flow sensors (also referred to as flow sensors or flow pickups).

For example, volume flow sensors are based on magnetic-inductive measuring principles or on ultrasound measuring methods.

The volume flow can also be determined indirectly by means of a throttle means or device, respectively, and pressure measurements in front of and behind the throttle means or device, respectively.

The volume flow measurement that can be required can be performed by analyzing balance signals of dialysis machines having balances for dialysate or substituate solution bags. Such an embodiment is, for example, known from the state of the art. Hereby, a flow sensor (or volume flow sensor, respectively) can advantageously be omitted.

Such a measurement can particularly be used for a dialysate or substituate solution of known density to the effect that a volume-per-time-signal (flow) may be derived from the (optionally transient) balance signal. An appropriate arrangement is shown in FIG. 5.

In one embodiment of the method according to the present invention, the rotation speed of the centrifugal pump is determined by means of the electrical power input of the centrifugal pump. Thereby, the power input can also depend on further parameters, such as, e.g., the feed rate and/or the viscosity of the fluid conveyed. Such parameters can likewise be considered. Correspondingly prepared means or devices, respectively, may be provided.

The rotation speed can be proportional to the electric input voltage of the centrifugal pump, the feed rate and/or the viscosity can be proportional to the input current. The electric power input is proportional to the input voltage and to the input current.

In other exemplary embodiments according to the present invention, the rotation speed is detected by means of Hall sensors detecting the magnetic field of a (permanent) magnet of the centrifugal pump.

Measurements of the rotation speed can also be determined by means of further methods known to a person skilled in the art, such as, for example, optical methods (e.g., stroboscopically), methods based on the law of induction (tachogenerator, induction transducers, etc.), and the like.

In other exemplary embodiments according to the present invention, the rotation speed of the pump is directly predetermined by the operating system. Thus, the rotation speed of the pump can be known.

According to the present invention, the pressure or a related information can be determined upstream of the centrifugal pump when parameters such as the pressure downstream of the centrifugal pump, the volume flow and/or the rotation speed of the centrifugal pump during operation are known. Thereby, instead of knowing the volume flow, in some exemplary embodiments of the method according to the present invention it is sufficient to know the power input of the centrifugal pump as well as, optionally, one additional value allowing a sufficiently unambiguous conclusion regarding the volume flow.

Instead of the rotation speed of the centrifugal pump, it is in other exemplary embodiments of the method according to the present invention likewise sufficient to have other values present or measured or detected that allow a sufficiently unambiguous conclusion to the rotation speed.

Detecting a value for the pressure upstream of the centrifugal pump can, for example, be carried out by calculation using values that can be derived from a set of characteristic curves (such as, for example, shown in FIG. 2) of the centrifugal pump used. Thereby, it is primarily referred to the value of the pressure difference usually read off the ordinate or y-axis, respectively. When knowing the pressure difference and a pressure value upstream of the centrifugal pump, the pressure downstream can be calculated, and vice versa. Knowing the volume flow thereby delivers information about the exact position of the characteristic curve in the graph and thus about the pressure difference.

For rotation speeds or rotation speed differences not plotted in form of characteristic curves in the respectively used set of characteristic curves, an approximated value can be determined by means of interpolation.

According to the present invention, the pressure or a related information upstream of the centrifugal pump can already be present or known when a hydrostatic pressure or the level of a liquid column up to the pump inlet is known. In those exemplary embodiments, a pressure sensor otherwise provided upstream can advantageously be omitted.

In one exemplary embodiment according to the present invention, the pressure of the medical fluid is determined in an extracorporeal volume flow.

The term "extracorporeal volume flow" as used herein refers to a volume flow outside a patient's body. The patient can be a human or an animal. According to the present invention, it is irrelevant if the patient is ill or healthy.

The extracorporeal volume flow can be a closed or an open circuit or loop, respectively.

The extracorporeal volume flow can have an arterial and/or a venous access to the body.

In a further exemplary embodiment, the pressure is determined while considering an information about the volume flow at the inlet or at the outlet of the centrifugal pump.

The pressure upstream or downstream of the centrifugal pump can be an overpressure or excess pressure, respectively, or a negative pressure.

In certain exemplary embodiments according to the present invention, the viscosity of the conveyed fluid is known. The viscosity can have an influence onto the characteristic curve of the pump. Knowing and considering the latter can advantageously enhance the accuracy of the method according to the present invention. A characteristic curve of the pump is, for example, shown in FIG. 4.

In some exemplary embodiments according to the present invention, the measurement of the viscosity is carried out by the pump itself as, for example, described in the European patent EP 1 284 415 B1, the respective disclosure of which is herein incorporated by reference in its entirety.

In certain exemplary embodiments according to the present invention, the relative or absolute viscosity measurement is carried out by using other means such as, for example, optical hematocrit measurements.

In some other exemplary embodiments of the present invention, the value of the viscosity is input into the system.

According to the substantial principles underlying the method according to the present invention, a related pressure difference can be read off by means of a set of characteristic curves of the (centrifugal) pump used and a volume flow known. After having measured a pressure value of the fluid in the fluid line in front of (upstream) or behind (downstream) the centrifugal pump, the pressure difference read off allows conclusions or a calculation, respectively, of the other pressure value of the fluid in the fluid line behind (downstream) or in front of (upstream) the centrifugal pump.

Alternatively, the principles underlying the method according to the present invention may be used to determine the volume flow or flux, respectively, of a medical fluid in a fluid line by using at least one centrifugal pump. Hereby, the pressure values of the fluid upstream and downstream of the centrifugal pump are detected. The pressure difference between these pressure values is calculated. Subsequently, the related volume flow or flux, respectively, of the fluid is detected by means of the set of characteristic curves and the related rotation speed of the pump. Also, this method, which is then a method for determining a volume flow, is subject-matter of the present invention. Exemplary embodiments hereof comprise one or more of the features and feature combinations herein given in any arbitrary paragraph of the specification as long as a person skilled in the art recognizes the said to be reasonable.

An object according to the present invention is further solved by means of an external medical functional device, in which the advantages achievable by means of the method according to the present invention may undiminishedly also be obtained by means of the external medical functional device according to the present invention.

In one exemplary embodiment, the external medical functional device according to the present invention is designed or embodied such that it comprises only one pressure sensor or one pressure measurement site downstream of the centrifugal pump for determining a pressure of a fluid upstream of the centrifugal pump or only one pressure sensor or one pressure measurement site upstream of the centrifugal pump for determining a pressure downstream of the centrifugal pump. Additional pressure sensors or pressure measurement sites for measuring a pressure of another fluid or of the same fluid at another site or in another state are thereby unaffected. Thus, the centrifugal pump can be arranged in the arterial leg of a blood circuit in order to determine the arterial pressure upstream of the centrifugal pump by using the method according to the present invention. Additionally, the system comprising the centrifugal pump may comprise further pressure sensors, e.g., venous pressure sensors, at other sites (e.g., in a venous leg of the blood circuit). This also applies for the treatment apparatus according to the present invention in some exemplary embodiments according to the invention of the latter.

In one exemplary embodiment, the external medical functional device according to the present invention comprises at least one rotating section or rotational section, respectively. In one exemplary embodiment according to the present invention, the latter is supported mechanically; in another embodiment, it is supported magnetically.

The rotational section can exclusively or additionally be supported magnetically.

The rotational section can be arranged in an interior of the medical functional device.

In one exemplary embodiment, the rotational section is an impeller or a rotor.

In a further exemplary embodiment, the external medical functional device according to the present invention comprises at least one rotational section provided or intended and embodied or designed, respectively, for being actuated or operated magnetically by means of an external actuation or by means of an electrical field.

In a further exemplary embodiment, the external actuation of the rotational section is designed to be actuated mechanically, e.g., by means of releasable fluid-tight couplings.

The magnetic actuation force of action or effect, respectively, can be achieved by means of one or more magnets. It can be achieved by means of current-conducting or live, respectively, conductors. For example, live coils can be used.

Such a magnetically actuated centrifugal pump can provide the advantage that a mechanical and/or electrical interface to the actuating apparatus or machine is not required and/or that no fluids have to be transmitted from the apparatus, such as, for example, a (medical) treatment apparatus, to the centrifugal pump.

In one exemplary embodiment of the present invention, the external medical functional device is designed or embodied as an external liquid circuit comprising a substitute, dialysate and/or an extracorporeal blood circuit.

In one exemplary embodiment of the present invention, the external medical functional device is designed or embodied as a blood or dialysate, respectively, cassette or as a combined blood/dialysate cassette.

In one exemplary embodiment according to the present invention, the external medical functional device is a disposable, a single use article or a one-use product.

In some exemplary embodiments according to the present invention the external functional device is a functional device which is not a permanent part of a treatment device but is added or attached or connected to it for the purpose of treatment "from outside" as an external part.

In one exemplary embodiment according to the present invention, the external medical functional device is a disposable cassette.

The disposable cassette can be a solid or hard part. It can be made from a plastic material. The disposable cassette can be produced by using an injection molding method.

Specifications concerning the further design of the external medical functional device according to the present invention in exemplary embodiments according to the invention are disclosed in the patent publication DE 10 2009 058 681 A1 of the applicant of the present invention that has been deposited at the German Patent and Trademark Office on Dec. 16, 2009 having the title "Bilanziereinrichtung, externe medizinische Funktionseinrichtung, Behandlungsvorrichtung sowie Verfahren", the respective disclosure of which is herein incorporated by reference in its entirety.

In certain exemplary embodiments according to the present invention the external medical functional device comprises at least or exactly one pressure sensor and/or at least or exactly one pressure sensor coupling site, particularly intended for executing the method according to the present invention.

In some exemplary embodiments according to the present invention the external medical functional device comprises at least or exactly one volume sensor and/or at least or exactly one volume sensor coupling site, particularly intended for executing the method according to the present invention.

In certain exemplary embodiments according to the present invention the external medical functional device is a blood cassette. In some exemplary embodiments according to the present invention the external medical functional device is a blood cassette for dialysis, in particular for hemodialysis.

An object according to the present invention is further solved by an arithmetic unit or processing unit, in which the advantages achievable by means of the method according to the present invention may undiminishedly also be obtained by means of the arithmetic unit according to the present invention.

The arithmetic or processing, respectively, unit can be a computer or a microprocessor that is able to detect and process, for example, measurement signals of the pressure upstream or downstream of the centrifugal pump, of the volume flow and/or of the rotation speed of the centrifugal pump and is configured herefor.

The arithmetic unit may also be used for processing the measurement signals and for forwarding or transferring or transmitting, respectively, data calculated therefrom in form of control signals to the centrifugal pump. This can, for example, be advantageous when the volume flow and/or the pressure measured and/or determined according to the present invention falls below or exceeds certain threshold values.

An object according to the present invention is further solved by a treatment apparatus, in which the advantages achievable by means of the method according to the present invention may undiminishedly also be obtained by means of the treatment apparatus according to the present invention.

The treatment apparatus according to the present invention is designed or embodied and configured for determining a pressure according to the method according to the present invention. Herefor, the treatment apparatus comprises in one exemplary embodiment according to the present invention an arithmetic unit that is suited and provided or intended or configured, respectively, to determine a pressure according to the method according to the present invention.

In one exemplary embodiment according to the present invention, the treatment apparatus is designed or embodied such that it comprises only one pressure sensor downstream of a centrifugal pump for determining a pressure upstream of the centrifugal pump or only one pressure sensor upstream of the centrifugal pump for determining a pressure downstream of the centrifugal pump.

In one exemplary embodiment according to the present invention, the treatment apparatus comprises at least one arterial line section, a centrifugal pump for conveying blood within the extracorporeal blood circuit and a venous line section.

In a further exemplary embodiment, the treatment apparatus is designed or embodied as a blood treatment apparatus, in particular as a hemodialysis apparatus.

In one exemplary embodiment of the treatment apparatus according to the present invention, the treatment apparatus comprises a device or means, respectively, intended or provided and configured for actuating the centrifugal pump via a magnetic actuation interface.

The device or means, respectively, can, for example, be or comprise a magnet or a magnetically acting system and/or a live conductor, such as, for example, one or more live coils.

An output device may be connected to the arithmetic unit in order to be able to display the pressure determined according to the present invention.

Even though not explicitly stated herein, the treatment apparatus according to the present invention comprises those devices or means, respectively, that are required for performing the method according to the present invention according to the respective embodiment thereof.

An object of the present invention is further solved by a digital storage means and/or a computer program product and/or a computer program, in which all advantages achievable by means of the method according to the present invention may likewise undiminishedly be obtained by means of the latter.

The digital storage means that can in particular be a disk, a CD or a DVD preferably comprises electrically readable control signals that can interact with a programmable computer system such that the execution of the technical steps of a method according to the present invention is prompted.

The computer program product preferably comprises a program code stored on a machine-readable storage means for prompting the execution of the technical steps of a method according to the present invention when executing the program product on a computer.

The term "machine-readable storage means" as used herein refers to a storage means comprising data or information interpretable by software and/or hardware. The storage means may be a data medium such as a disk, a CD, DVD, and the like.

The computer program comprises a program code for prompting the execution of the technical steps of the method according to the present invention when executing the program on a computer.

By means of the present invention, it is advantageously possible to determine two pressures at practically one point of time by using only one pressure sensor or generally only one pressure measuring site. Thus, according to the present invention, an additional second pressure may advantageously be determined by using only one pressure sensor as compared to the state of the art. For determining two pressures (upstream and downstream), one pressure sensor may alternatively be omitted. The latter contributes to reducing the effort and costs for manufacturing. As artifacts or false displays resulting from the second pressure sensor that is not required according to the present invention may be avoided, the quality of the pressure measurement may advantageously be increased.

In practice, primarily pressure measurement devices that have measured in the range of certain negative pressures (such as is usually the case in the arterial leg of an extracorporeal circuit) have repeatedly shown technical insufficiencies due to a loss of contact between the pressure pickup and the pressure transducer such as a membrane, or the like. Advantageously, no such insufficiencies are observed when using the present invention as one pressure sensor less is used (the one which would otherwise particularly measure negative pressures).

In the state of the art, such insufficiencies had often to be remedied by means of specific technical effort. According to the present invention, this effort can advantageously be avoided.

Moreover, due to omitting a further pressure sensor or a further pressure measurement site, the dimensions of the external medical functional device or its required space, respectively, can advantageously be kept small.

Due to a magnetic support of the centrifugal pump, the construction of the external medical functional device may advantageously be simplified. Thus, it can advantageously be possible to omit mechanical elements or components, respectively, such as bearings and the like, and to thus advantageously ensure little wear of the elements and/or little abrasive wear. This advantageously also allows one to avoid or reduce a heating of the centrifugal pump.

The magnetic actuation interface for operating the centrifugal pump or a rotational section thereof, respectively, may advantageously provide a contactless and/or seal-free actuation of the centrifugal pump. In this way, it can advantageously be possible to omit open interfaces between the centrifugal pump and the treatment apparatus.

An—albeit only extremely small—contamination risk of the medical fluids can thus advantageously be reduced or even completely excluded.

Executing the method according to the present invention by the external functional device according to the present invention may allow for a cost efficient manufacturing of the parts used, e.g. sensors or pump sections by combining some or all functions and/or the parts necessary therefore on one blood cassette, in particular on one blood cassette for dialysis, more particularly for hemodialysis.

In some exemplary embodiments according to the present invention combining as described above may moreover advantageously allow an easier arrangement of all or some parts necessary for executing the method according to the present invention on the treatment device, since these parts are arranged together.

In certain exemplary embodiments according to the present invention combining as described above may additionally advantageously allow a comparatively secure insertion of all or some parts necessary for executing the method according to the present invention in or on the treatment device. This may be ensured by their arrangement in or on the external functional device under certain distances, under certain interconnections between them or with other parts, etc.

In the following, the present invention will be described exemplarily with respect to the attached drawings. In the drawings, identical reference numerals refer to the same or identical elements.

DETAILED DESCRIPTION

Figure 1:
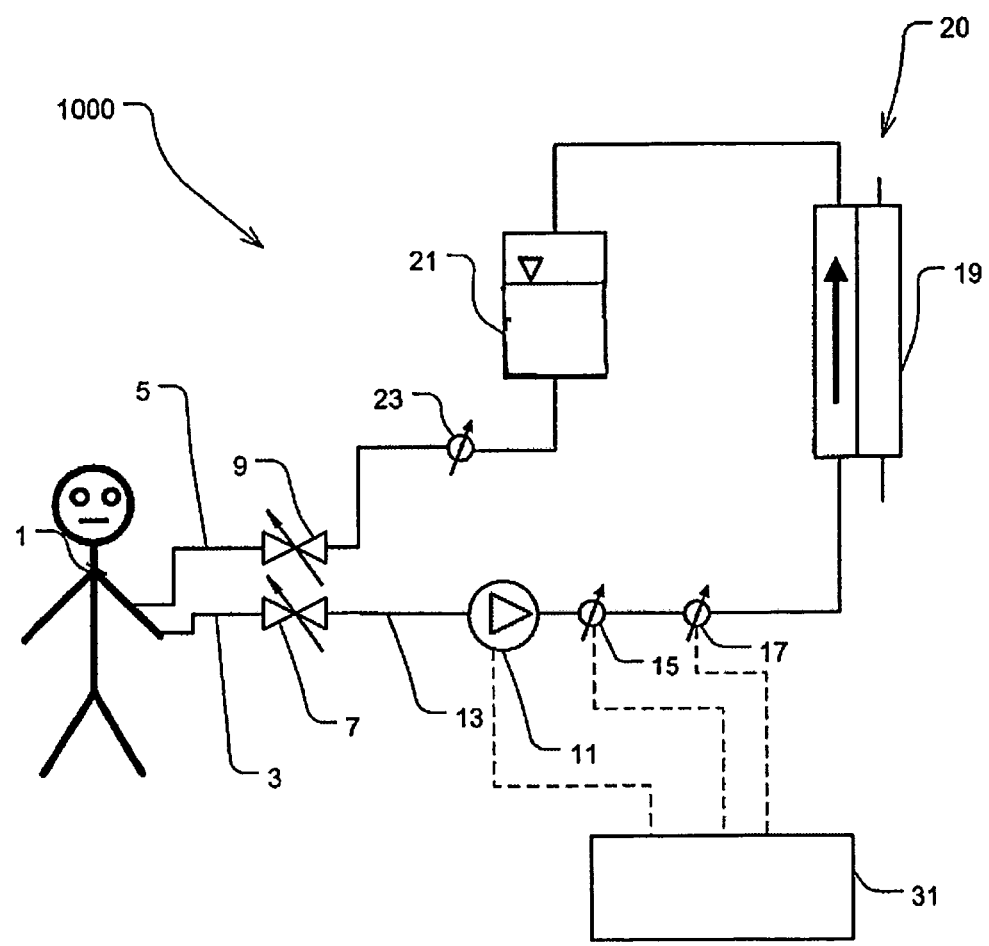
FIG. 1 shows, in a schematically simplified manner, an extracorporeal blood circuit comprising a centrifugal pump for performing the method according to the present invention.

FIG. 1 shows an extracorporeal blood circuit 1000 for performing the method according to the present invention on a patient 1 in a schematically simplified manner.

The extracorporeal blood circuit 1000 comprises an arterial leg or arterial line section 3, respectively, as well as a venous leg or venous line section 5, respectively. An arterial shut-off valve 7 is arranged in the arterial line section 3 of the extracorporeal blood circuit 1000; a venous shut-off valve 9 is arranged in the venous line section 5 of the extracorporeal blood circuit 1000.

A centrifugal pump 11 generates the required perfusion pressure for the flow through the extracorporeal blood circuit 1000. Depending on the pressure relations in the arterial line section 3 and in a suction area 13, a negative pressure can be generated in the suction area 13.

A pressure sensor 15 measures the pressure downstream of the centrifugal pump 11 that is substantially generated or built up, respectively, by the centrifugal pump 11. In this arrangement, the said pressure is at the same time the inlet pressure for the subsequent blood treatment device 19, for example, a hemodialyzer, of a treatment apparatus 20 according to the present invention that is represented only in sections.

A volume flow sensor 17 is arranged downstream of the pressure sensor 15 in the extracorporeal blood circuit 1000. The volume flow sensor may, for example, be a magnetic-inductive sensor or an ultrasound sensor.

A venous drip chamber 21 is arranged downstream of the blood treatment device 19.

A venous pressure sensor 23 is arranged between the venous drip chamber 21 and the venous shut-off valve 9.

According to the present invention, in order to be able to determine the pressure upstream of the centrifugal pump 11, no arterial pressure sensor has to be arranged in the suction area 13 or upstream of the centrifugal pump 11, respectively. According to the present invention, this pressure upstream of the centrifugal pump 11 is rather determined by using information about the volume flow, the pressure downstream of the centrifugal pump 11 and the rotation speed thereof.

FIG. 1 furthermore shows an arithmetic unit 31 which is used for determining the pressure according to the method according to the present invention.

Figure 2:
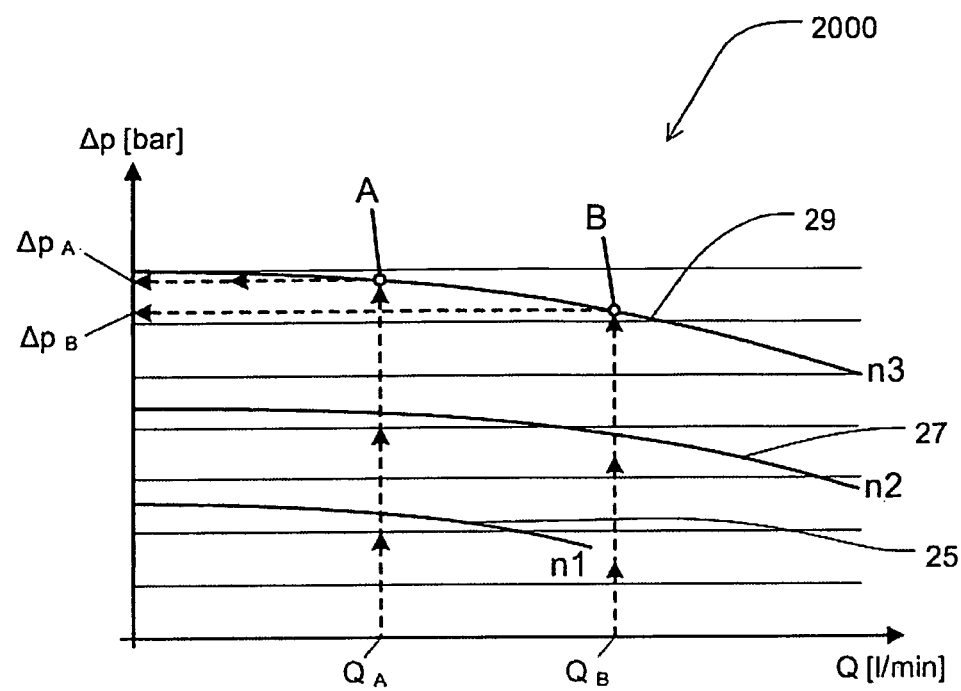
FIG. 2 exemplarily shows a set of characteristic curves of a centrifugal pump.

In order to facilitate understanding, the following discussion of FIG. 2 refers to the devices or means, respectively, shown in FIG. 1 but not again shown in FIG. 2.

FIG. 2 exemplarily shows a set 2000 of characteristic curves of the centrifugal pump 11.

The set 2000 of characteristic curves describes the operating characteristics of the centrifugal pump 11 and has been detected experimentally at an earlier point of time. Three characteristic curves each for one rotation speed n1 (reference numeral 25), n2 (reference numeral 27) and n3 (reference numeral 29) are exemplarily shown.

In order to illustrate the determination according to the present invention of the pressure upstream of the centrifugal pump 11 in the suction area 13, two operating points A and B of the centrifugal pump 11 in the set 2000 of characteristic curves are exemplarily discussed.

By means of a control unit of the centrifugal pump 11, also serving as an arithmetic unit 31 for receiving and processing the different measurement parameters a predetermined or desired volume flow, e.g., $Q_A$, is set that can also be measured by means of the volume flow sensor 17. When the desired volume flow $Q_A$ has been reached, the centrifugal pump 11 rotates with a rotation speed correlating thereto, for example, with the rotation speed n3 (reference numeral 29).

By means of the characteristic line of the set 2000 of characteristic curves related to the rotation speed n3, the pressure difference $\Delta p_A$ can now be read off at the ordinate. The pressure at the outlet or downstream of the centrifugal pump 11 is measured by means of the pressure sensor 15. The pressure upstream or at the inlet of the centrifugal pump 11 in the suction area 13 can now be determined or calculated, respectively, according to the present invention.

The following further exemplary calculation again points out this proceeding: The centrifugal pump 11 is in this example operated with a rotation speed of 3000 U/min and this results in a volume flow of approx. 300 ml/min. By means of the characteristic line, a pressure difference $\Delta p$ of about 260 mbar is read off at the ordinate. Furthermore, the pressure downstream of the centrifugal pump 11 is measured to be 200 mbar. Herefrom, the pressure upstream of the centrifugal pump 11 can be determined to be −60 mbar (pressure difference $\Delta p$=p downstream minus p upstream; 260 mbar=200 mbar−p upstream).

In all cases, corresponding control parameters including consideration of disturbance variables can be integrated in the regulation or control of the flow through the extracorporeal blood circuit 1000 and/or in the actuation control of the centrifugal pump 11.

Figure 3:
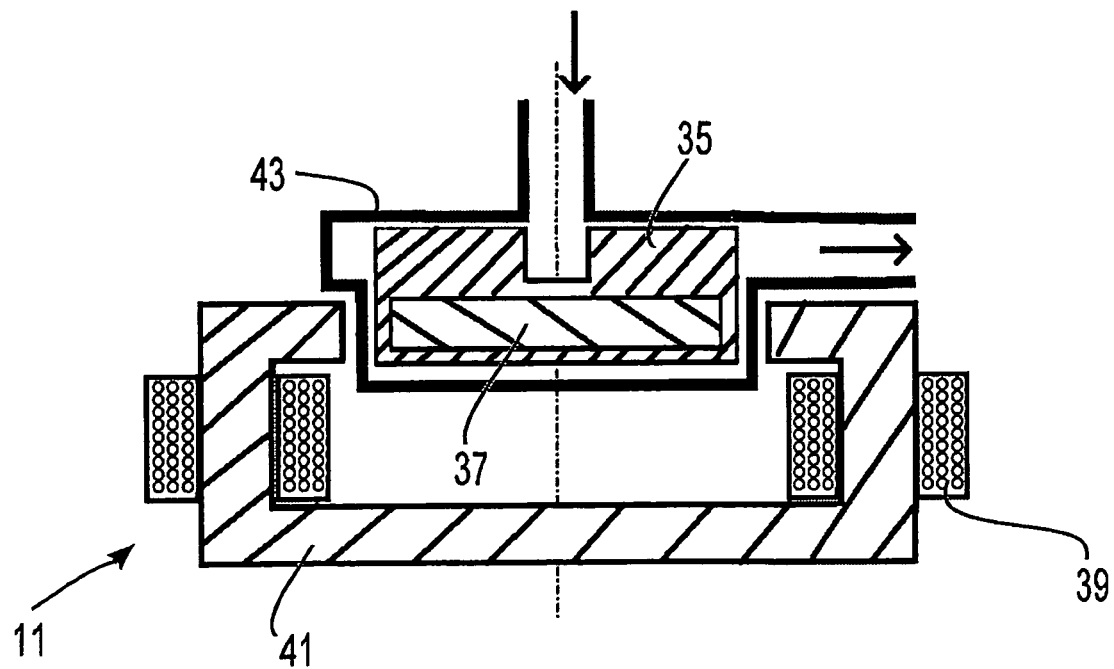
FIG. 3 shows, in a schematically simplified manner, a centrifugal pump comprising a magnetic support and a magnetic actuation.

FIG. 3 shows a centrifugal pump 11 comprising a rotor 35 as a rotational section, a permanent magnet 37 embedded in the rotor 35, coils 39 and a stator 41. The centrifugal pump 11 comprises a housing 43 comprising an inlet and an outlet (indicated by means of arrows in FIG. 3).

The centrifugal pump 11 is flown through in the flow direction shown. The actuation of the rotor 35 is effected by means of a circumferential electromagnetic field generated by actuating the coils 39 of the stator 41.

One or more impeller magnets or at least ferromagnetic materials can be integrated in or at, respectively, the rotor 35.

The support of the rotor 35 can then, on the one hand, be carried out by means of the impeller magnets and, on the other hand, by means of magnets provided outside the centrifugal pump 11. The magnets can be arranged circumferentially in the same movement of rotation as the rotor 35. Instead of the circumferential magnets or in addition hereto, also a circumferential electromagnetic field in a coil arrangement can support the rotor 35 or fixate the said in a stable circumferential position, respectively. Though not shown in the figures, this exemplary embodiment is encompassed by the invention as well.

Figure 4:
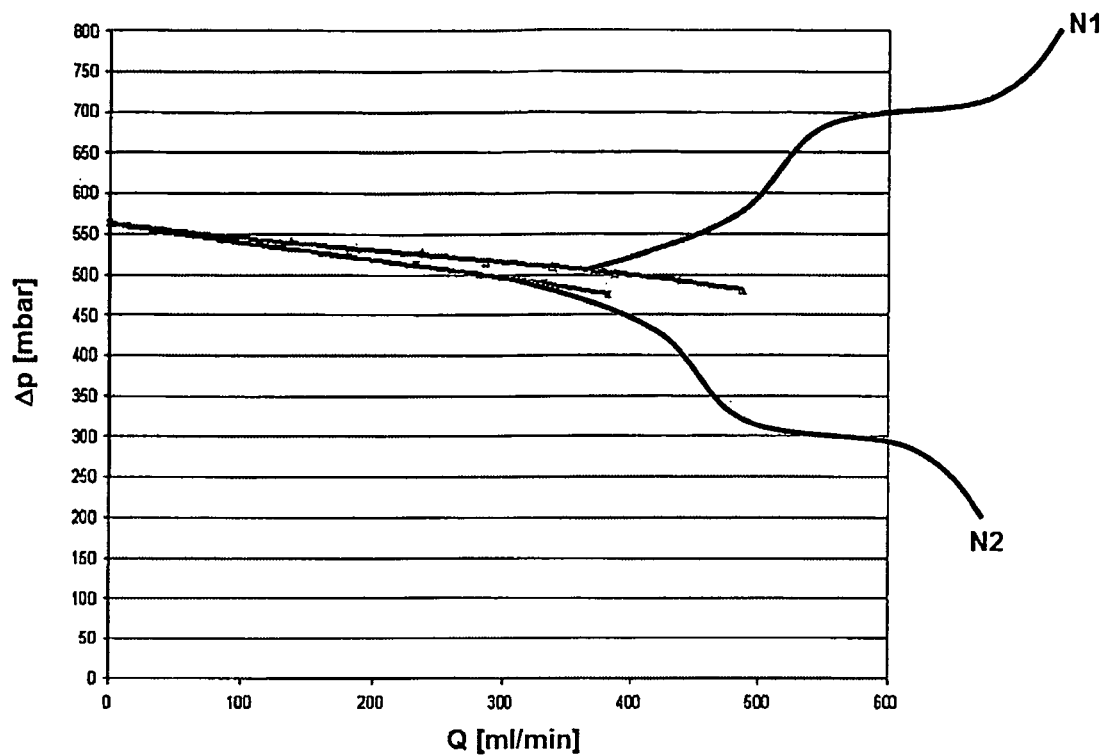
FIG. 4 shows characteristic curves of a centrifugal pump plotted against the viscosity of a fluid.

FIG. 4 shows characteristic curves N1 and N2 (it applies: $\Delta P = f(V)$) of the centrifugal pump 11 plotted against the dynamic viscosity of a fluid. The unit of the viscosity is given in centipoises (cP; 1 cP=$10^{-3}$ kg/ms, alternatively mPa*s).

The measurement values of the characteristic curve N1 have been detected at a viscosity of 3 cP. The characteristic curve N1 connecting the measurement values has been approximated to the measurement values by using polynomial formation.

The measurement values of the characteristic curve N2 have been detected at a viscosity of 5 cP. The characteristic curve N2 connecting the measurement values has also been approximated to the measurement values by using polynomial formation.

Figure 5:
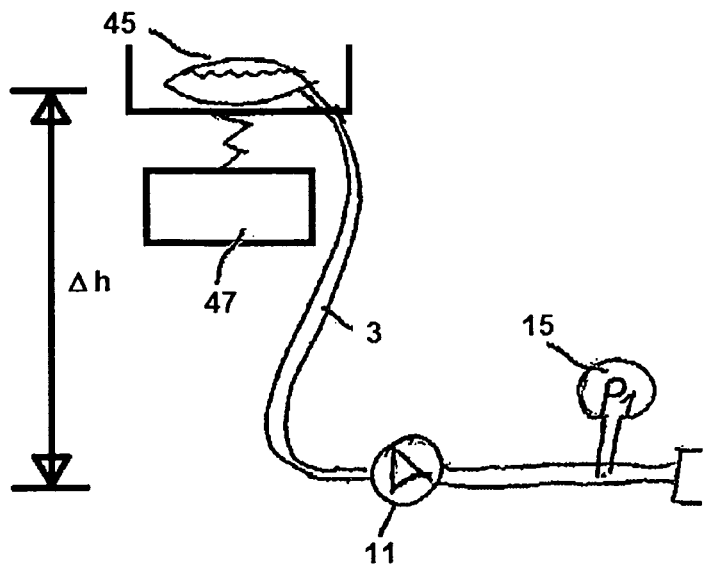
FIG. 5 schematically shows an arrangement for measuring the volume flow.

FIG. 5 schematically shows an arrangement for volume flow measurements.

As shown in FIG. 5, the arterial line section 3 is connected to a solution bag 45. The solution bag 45 may contain substituate solution or dialysate solution.

A balance 47 is connected to the solution bag 45.

For determining the absolute pressure downstream of the pump, a pressure sensor upstream of the centrifugal pump 11 can be omitted. There is solely provided pressure sensor 15 downstream.

This pressure sensor 15 can also be omitted in dialysis machines comprising balances for dialysate or substituate solution bags when the level of the liquid column up to the pump's inlet is known. This circumstance results from the hydrostatic pressure that may be calculated according to $$p(h)=\rho*g*h$$

wherein:
p(h)=hydrostatic pressure as a function of the water level; [p]=Pa;
g=acceleration of gravity; $[g]=m/s^2$;
$\rho$=density (water: $\rho=1000$ kg/m$^3$); $[\rho]=kg/m^3$;
h=level of the liquid column; [h]=m;

The density of the solution liquid depends on the solution temperature. Usually, the said temperature is 37° C. in order to neither draw heat from the patient nor heat the patient. The density can thus be regarded as being constant and known.

In exceptional cases (overheating, hypothermia), heat can be drawn from the patient or supplied to the patient by modifying the solution temperature. The amount of the respective difference in temperature is, however, in a range of preferably smaller than 2° C., in particular preferably smaller than 1° C. The density can sufficiently exactly be regarded to be constant within these limits; moreover, the dependency of the solution density from the temperature could be deposited as a function in the arithmetic unit 31 of the treatment apparatus 20 or at another site and could be considered when calculating the hydrostatic pressure.

The invention claimed is:

1. A method for determining a pressure of a medical fluid in a fluid line in a closed circuit by using at least one centrifugal pump and only one pressure sensor, the method comprising:
measuring a pressure upstream or downstream of the centrifugal pump by the only one pressure sensor at one rotation speed; and
determining a pressure downstream of the centrifugal pump based on the measured pressure upstream of the centrifugal pump, a predetermined volume flow in the fluid line, and the one rotation speed of the centrifugal pump, or determining a pressure upstream of the centrifugal pump based on the measured pressure downstream of the centrifugal pump, a predetermined volume flow in the fluid line, and the one rotation speed of the centrifugal pump.

2. The method according to claim 1, wherein the pressure of the medical fluid is determined in an extracorporeal volume flow.

3. The method according to claim 1, wherein the predetermined volume flow in the fluid line is a volume flow at an inlet or at an outlet of the centrifugal pump.

4. The method according to claim 1, wherein the medical fluid is selected from the group consisting of dialysate liquid, substituate liquid, drugs, blood, and combinations thereof.

5. An external medical functional device configured to perform the method according to claim 1, comprising:
the at least one centrifugal pump; and
the only one pressure sensor, wherein the only one pressure sensor is located downstream of the centrifugal pump for determining a pressure upstream of the centrifugal pump, or is located upstream of the centrifugal pump for determining a pressure downstream of the centrifugal pump.

6. An external medical functional device configured to perform the method according to claim 1, wherein the external medical functional device is designed or embodied as an external or extracorporeal blood circuit and/or a blood cassette.

7. The external medical functional device according to claim 6, wherein the external medical functional device is designed or embodied as a disposable or one-use article for insertion in a blood treatment apparatus.

8. An arithmetic unit comprising an arithmetic unit configured to determine a pressure according to the method of claim 1.

9. A treatment apparatus for treating medical fluids comprising a treatment apparatus configured to determine a pressure of a medical fluid in a fluid line in a closed circuit by using at least one centrifugal pump and only one pressure sensor, the treatment apparatus comprising:
the only one pressure sensor, wherein the only one pressure sensor is configured to measure a pressure upstream or downstream of the centrifugal pump at one rotation speed; and
an arithmetic unit configured to determine a pressure downstream of the centrifugal pump based on the measured pressure upstream of the centrifugal pump, a predetermined volume flow in the fluid line, and the one rotation speed of the centrifugal pump, or to determine a pressure upstream of the centrifugal pump based on the measured pressure downstream of the centrifugal pump, a predetermined volume flow in the fluid line, and the one rotation speed of the centrifugal pump.

10. The treatment apparatus according to claim 9, further comprising a device configured to actuate the centrifugal pump via a magnetic actuation interface.

11. The treatment apparatus according to claim 10, wherein the treatment apparatus is functionally connected to an external medical functional device.

12. The treatment apparatus according to claim 9, wherein the treatment apparatus is designed or embodied as a blood treatment apparatus.

13. The treatment apparatus according to claim 12, wherein the blood treatment apparatus is a hemodialysis apparatus.

14. A non-transitory computer-readable medium with an executable program stored thereon, wherein the program is configured to instruct a programmable computer system to execute a method for determining a pressure of a medical fluid in a fluid line in a closed circuit by using at least one centrifugal pump and only one pressure sensor, the method comprising:
measuring a pressure upstream or downstream of the centrifugal pump by the only one pressure sensor at one rotation speed; and
determining a pressure downstream of the centrifugal pump based on the measured pressure upstream of the centrifugal pump, a predetermined volume flow in the fluid line, and the one rotation speed of the centrifugal pump, or determining a pressure upstream of the centrifugal pump based on the measured pressure downstream of the centrifugal pump, a predetermined volume flow in the fluid line, and the one rotation speed of the centrifugal pump.

15. The non-transitory computer-readable medium according to claim 14, wherein the non-transitory computer-readable medium is selected from the group consisting of a disk, a CD, or a DVD.

* * * * *